United States Patent [19]

Pickett

[11] Patent Number: 5,567,850
[45] Date of Patent: Oct. 22, 1996

[54] METHOD FOR MAKING ACYL SUBSTITUTED RESORCINOLS

[75] Inventor: James E. Pickett, Schenectady, N.Y.

[73] Assignee: General Electric Company, Schenectady, N.Y.

[21] Appl. No.: 336,135

[22] Filed: Nov. 8, 1994

[51] Int. Cl.$^6$ ................................................. C07C 45/45
[52] U.S. Cl. ............................................................ 568/322
[58] Field of Search ..................................... 568/315, 322

[56] References Cited

U.S. PATENT DOCUMENTS

| | | | |
|---|---|---|---|
| 2,794,052 | 5/1957 | Gordon et al. | 568/315 |
| 2,891,996 | 6/1959 | Clark | 568/315 |
| 3,526,666 | 9/1970 | Powder | 568/315 |
| 3,769,349 | 10/1973 | Yukutomi et al. | 568/322 |
| 4,400,542 | 8/1983 | Rainey et al. | 568/315 |
| 4,990,680 | 2/1991 | Neumann et al. | 568/322 |

OTHER PUBLICATIONS

Anjaneyulu et al, Chem. Abst., vol. 109, #54433c (1988).
Olah, "Freidel Crafts & Related Reactions", vol. #III, pp. 46–48 (1964).
Pearson et al., Synthesis, "Friedel–Crafts Acylations With Little Or No Catalyst" (1972), pp. 533–542.
Doebner et al., Chemiche Berichte, 11, (1878), pp. 2268–2272.
Panaitescu et al., Rev. Chim. 16 (8), "Synthesis of Dibenzoylresorcinol, Absorber of UV Radiations" (1965), pp. 361–365.
Sharma et al., Monatshefte fur Chemie 116, "Photo–Fries Rearrangement: Rearrangement of Benzoyloxy Compounds" (1985), pp. 353–356.
Zemzina et al., J. Org. Chem. USSR, 6, "Mono– and Dibenzoylation of m–Dimethoxybenzene" (1972), pp. 529–531.

*Primary Examiner*—James H. Reamer
*Attorney, Agent, or Firm*—Edward A. Squillante, Jr.; William H. Pittman

[57] ABSTRACT

A method for making acyl substituted resorcinols is disclosed and the method comprises the step of contacting resorcinols and acid halides in the presence of catalytic amounts of transition metal Lewis acids.

12 Claims, No Drawings

METHOD FOR MAKING ACYL SUBSTITUTED RESORCINOLS

FIELD OF THE INVENTION

This invention relates to a novel method for making acyl substituted resorcinols. More particularly, the instant invention is directed to a method for making acyl substituted resorcinols by contacting resorcinols and acid halides in the presence of catalytic amounts of transition metal Lewis acids.

BACKGROUND OF THE INVENTION

Thermoplastic resins are generally characterized by their many advantageous properties which include optical clarity, high ductility, high heat deflection temperature as well as dimensional stability. As a result of such properties, they are often employed in many commercial applications.

While thermoplastic resins possess the above-described advantageous properties, they often display low abrasion and chemical solvent resistances, and like many other organic polymeric materials, they are susceptible to photodegradation by ultraviolet light. The photodegradation typically results in unfavorable characteristics including yellowing and erosion of the resin surface.

Diacyl resorcinols, particularly dibenzoyl resorcinols, have been found to be effective light stabilizers in polymer resins. Typically, dibenzoyl resorcinols are prepared by treating dimethoxybenzene with benzoyl chloride in the presence of at least stoichiometric amounts of anhydrous aluminum chloride in an organic solvent. However, such a method is not very favorable, since among other reasons, it results in the release of environmentally unfriendly organic volatiles and requires disposal of large amounts of excess aluminum chloride as well as by-products thereof.

It is of increasing interest to prepare acyl substituted resorcinols by a method which does not, for instance, encourage the release of environmentally unfriendly organic volatiles.

The instant invention, therefore, is directed to a novel method for making acyl substituted resorcinols while minimizing environmentally unfriendly side effects.

DESCRIPTION OF THE PRIOR ART

Efforts for preparing dibenzoyl resorcinols have been disclosed. In U.S. Pat. 2,794,052, dibenzoyl resorcinols are prepared by subjecting dialkyl ethers to acyl chlorides and at least stoichiometric amounts of aluminum chloride and the use of resorcinols as a starting material is discouraged.

Still other efforts have been disclosed for producing dibenzoyl resorcinols. In Sharma et al., Monatsh Chem. 116, pp. 353–356 (1985), dibenzoyl resorcinol is prepared via the photochemical Fries rearrangement of resorcinol dibenzoate to a benzoate ester of 2,4-dihydroxy benzophenone and subsequently dibenzoyl resorcinol.

Additionally, in Pearson et al., Synthesis, pp. 533–542 (1972), methods of employing Lewis acids including ferric chloride, iron powder, iodine and zinc chloride are disclosed. However, said methods are directed to Friedel-Craft acylations describing the reaction of resorcinol and acetic anhydride to produce 2,4dihydroxyacetophenone.

The instant invention is patentably distinguishable from the above-described, since among other reasons, it is directed to a novel method for making acyl substituted resorcinols by contacting resorcinols and acid halides in the presence of catalytic amounts of transition metal Lewis acids.

SUMMARY OF THE INVENTION

The instant invention is directed to a novel method of making acyl substituted resorcinols, said method comprises the step of contacting:

(a) resorcinols;

(b) acid halides; and (c) catalytic amounts of transition metal Lewis acids.

DETAILED DESCRIPTION OF THE PREFERRED EMBODIMENTS

In the instant invention, the resorcinols typically employed are represented by the formula

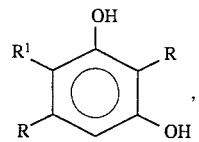

wherein each R is independently hydrogen or a $C_{1-10}$ hydrocarbon and $R^1$ is hydrogen or an acyl group and preferably a benzoyl group and the preferred resorcinols employed in the instant invention are 1,3-dihydroxybenzene and 2,4-dihydroxybenzophenone.

The acid halides employed typically have the formula

wherein A is a substituted or unsubstituted aromatic radical and preferably a phenyl group and X is a halogen and preferably chlorine.

The catalyst employed is a transition metal Lewis acid and the resulting product obtained in the instant invention is an acyl substituted resorcinol and preferably 4,6-dibenzoyl-resorcinol. Illustrative examples of transition metal Lewis acids employed include cadmium chloride and iron chloride. However, the most preferred transition metal Lewis acid employed in this invention is zinc chloride. Furthermore, it is within the scope of the instant invention to employ mixtures of the above-described transition metal Lewis acids to catalyze the reaction.

The instant novel method reveals many new and unexpected results which include the discovery that catalytic amounts of transition metal Lewis acids may be employed when resorcinols are subjected to and reacted with acid halides to afford acyl substituted resorcinols and particularly 4,6-diacyl substituted resorcinols. The reaction occurs in a single step and does not require the use of organic solvents for acyl substituted resorcinol formation since such a reaction takes place in the melt. Moreover, when $R^1$ is not an acyl group, diacyl substitutions are unexpectedly observed.

As previously stated, this invention comprises the step of contacting resorcinols and acid halides in the presence of catalytic amounts of transition metal Lewis acids to produce a reaction mixture. There is no limitation with respect to the order in which the reactants and catalyst are added; however, the order of addition may alter the color but not the yield of the acyl substituted resorcinols obtained. The reaction mixture is typically heated to a temperature in the range of about 120° C. to about 250° C. and preferably in the range of about 150° C. to about 220° C. and most preferably in the range of about 170° C. to about 220° C. Additionally, it is noted herein that heating may begin prior to, during or after the reactants and catalyst are combined.

The amount of transition metal Lewis acid (catalyst) required in the instant invention is not stoichiometric and it is typically about 0.1 to about 50.0 mole percent and preferably about 1.0 to about 30.0 mole percent and most preferably about 5.0 to 15.0 mole percent based on total moles of resorcinol employed. Additionally, about 2 moles of acid halide are employed for every mole of resorcinol employed when $R^1$ is not an acyl group and about 1 mole of acid halide is employed for every mole of resorcinol when $R^1$ is an acyl group.

Once the reaction mixture is obtained, an esterification occurs and the resorcinols are converted to ester intermediates. The ester intermediates then subsequently and spontaneously rearrange to form the desired acyl substituted resorcinols in the reaction product. Further, it is within the scope of the instant invention to recrystallize the reaction product with organic solvents in order to obtain substantially pure acyl substituted resorcinols. Often, the product obtained after work-up is at least about 95% pure.

The following examples further illustrate and facilitate the understanding of the above-described novel method. The acyl substituted resorcinols obtained may be confirmed via conventional techniques including proton and carbon-13 nuclear magnetic resonance spectroscopy, infrared spectroscopy and GLC analysis.

EXAMPLE 1

A 100 mL round-bottomed flask equipped with a magnetic stirring bar, gas scrubber and oil bath heater at 120° C. was charged with 0.54 g (4 mmol) of anhydrous zinc(II) chloride (5 mole percent based on total resorcinol) and 19.0 mL (164 mmol) of benzoyl chloride to produce a catalyst mixture. 8.80 g (80 mmol) of 1,3dihydroxybenzene was added to the catalyst mixture in portions over several minutes to produce a reaction mixture. The temperature was then raised to about 205° C. over the course of 20 minutes and held at that temperature for 1 hour. A sample of the reaction mixture was removed for NMR spectroscopy. Results showed approximately 60% conversion to 4,6-dibenzoyl resorcinol. The reaction mixture was cooled to 120° C. and 40 mL of glacial acetic acid were added. The reaction mixture was further cooled to 80° C. and 20 mL of absolute ethanol were added. The resulting mixture was transferred to a beaker and allowed to cool to 5° C. in a refrigerator. A solid was recovered via filtration, washed with about 50 mL of cold ethanol and dried to give orange plates of 4,6-dibenzoyl resorcinol (11.80g 46% yield). Recrystallization from a mixture of 50 mL of ethanol and 15 mL chlorobenzene gave 10.8 g (42% yield) of pale yellow 4,6-dibenzoyl resorcinol.

EXAMPLE 2

Example 2 was prepared in a manner similar to the one described in Example 1 except that 2,4-dihydroxybenzophenone was employed in lieu of 1,3-dihydroxybenzene and 82 mmol of benzoyl chloride were used and 10 mole percent of anhydrous zinc(II) chloride was used based on total resorcinol. 10.6g (42%) of substantially pure 4,6-dibenzoyl resorcinol was recovered after recrystallization.

The data in the table below is provided to further confirm the unexpected results obtained in the instant invention. All entries have been prepared in a manner similar to the one described in the examples above.

TABLE

| Entry | Lewis Acid (%)[a] | Reaction Time at 200° C. | Yield[b] |
|---|---|---|---|
| 1 | 5.0 | 60 min | 60.0% |
| 2 | 10.0 | 40 min | 67.0% |
| 3 | 25.0 | 40 min | 67.0% |
| 4 | 10.0 | 60 min | 1.0% |

TABLE-continued

| Entry | Lewis Acid (%)[a] | Reaction Time at 200° C. | Yield[b] |
|---|---|---|---|
| 5 | 0.1 | 90 min | 8.0% |
| 6 | 1.0 | 60 min | 48.0% |
| 7 | 10.0 | 60 min | 61.0%. |

[a]Entries 1–3 employed $ZnCl_2$; entry 4 employed $CdCl_2$; entries 5–7 employed $FeCl_3$ and entry 8 employed $AlCl_3$.
[b]Determined by NMR analysis of reaction mixture

What is claimed is:

1. A method for making acyl substituted resorcinols, said method comprises the step of contacting:
   (a) resorcinols;
   (b) acid halides; and
   (c) a catalytic amount of transition metal Lewis acids, wherein said catalytic amount is about 0.1 to about 50.0 mole percent of said transition metal Lewis acids based on total moles of resorcinol employed.

2. A method for making acyl substituted resorcinols in accordance with claim 1 wherein said resorcinols in (a) have the formula

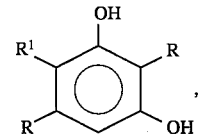

wherein each R is independently hydrogen or a $C_{1-10}$ hydrocarbon and $R^1$ is hydrogen or an acyl group.

3. A method for making acyl substituted resorcinols in accordance with claim 2 wherein said acyl group is a benzoyl group.

4. A method for making acyl substituted resorcinols in accordance with claim 3 wherein said resorcinol is 1,3-benzenediol or 2,4-dihydroxybenzophenone.

5. A method for making acyl substituted resorcinols in accordance with claim 1 wherein said acid halides have the formula

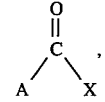

wherein A is an aromatic radical and X is a halogen.

6. A method for making acyl substituted resorcinols in accordance with claim 5 wherein said acid halides are benzoyl chloride.

7. A method for making acyl substituted resorcinols in accordance with claim 1 wherein said transition metal Lewis acids are $CdCl_2$ or $FeCl_3$.

8. A method for making acyl substituted resorcinols in accordance with claim 1 wherein said transition metal Lewis acid is $ZnCl_2$.

9. A method for making acyl substituted resorcinols in accordance with claim 1 wherein said contacting is a melt reaction at a temperature of about 120° C. to about 250°C.

10. A method for making acyl substituted resorcinols in accordance with claim 1 wherein said acyl substituted resorcinols are 4,6-acyl substituted resorcinols.

11. A method for making acyl substituted resorcinols in accordance with claim 10 wherein said 4,6-acyl substituted resorcinols are 4,6-dibenzoyl resorcinols.

12. A method for making acyl substituted resorcinols in accordance with claim 11 wherein said method further comprises a recrystallization step.

* * * * *